United States Patent
De Rosa et al.

(10) Patent No.: US 10,675,270 B2
(45) Date of Patent: Jun. 9, 2020

(54) CHONDROITIN COMPLEXES FOR TRANSCUTANEOUS ABSORPTION

(71) Applicant: Altergon S.A., Lugano (CH)

(72) Inventors: Mario De Rosa, Lugano (CH); Chiara Schiraldi, Lugano (CH)

(73) Assignee: Altergon S.A., Lugano (CH)

( * ) Notice: Subject to any disclaimer, the term of this patent is extended or adjusted under 35 U.S.C. 154(b) by 8 days.

(21) Appl. No.: 16/124,269

(22) Filed: Sep. 7, 2018

(65) Prior Publication Data

US 2019/0000803 A1 Jan. 3, 2019

Related U.S. Application Data

(62) Division of application No. 14/416,669, filed as application No. PCT/EP2013/065733 on Jul. 25, 2013, now abandoned.

(30) Foreign Application Priority Data

Jul. 27, 2012 (IT) .............................. MI2012A1316

(51) Int. Cl.
| | |
|---|---|
| *A61K 47/36* | (2006.01) |
| *A61K 31/407* | (2006.01) |
| *A61K 47/61* | (2017.01) |
| *A61K 9/00* | (2006.01) |
| *A61K 9/06* | (2006.01) |
| *A61K 8/73* | (2006.01) |
| *A61Q 19/08* | (2006.01) |
| *A61K 31/196* | (2006.01) |

(52) U.S. Cl.
CPC ............ *A61K 31/407* (2013.01); *A61K 8/735* (2013.01); *A61K 9/0014* (2013.01); *A61K 9/06* (2013.01); *A61K 31/196* (2013.01); *A61K 47/36* (2013.01); *A61K 47/61* (2017.08); *A61Q 19/08* (2013.01); *A61K 2800/54* (2013.01)

(58) Field of Classification Search
CPC .............. A61K 47/4823; A61K 31/196; A61K 31/407; A61K 9/0014; A61K 9/06; A61K 2800/54

USPC .......................................................... 514/54
See application file for complete search history.

(56) References Cited

U.S. PATENT DOCUMENTS

| | | | |
|---|---|---|---|
| 4,489,065 A * | 12/1984 | Walton ................ | A61K 31/715 514/34 |
| 6,051,587 A | 4/2000 | Dakashinamurti et al. | |
| 6,221,377 B1 | 4/2001 | Meyer | |
| 6,482,401 B1 | 11/2002 | Knigge | |
| 2003/0104601 A1 | 6/2003 | DeAngelis | |
| 2006/0084604 A1 * | 4/2006 | Kitaura ................ | A61K 9/0014 514/7.2 |
| 2011/0244520 A1 * | 10/2011 | Doherty ............... | C07K 14/245 435/84 |
| 2012/0094951 A1 | 4/2012 | Robinson | |

FOREIGN PATENT DOCUMENTS

| | | |
|---|---|---|
| EP | 1582214 A2 | 10/2005 |
| EP | 2106798 A1 | 10/2009 |
| JP | 2010173990 A | 8/2010 |

OTHER PUBLICATIONS

Office Action issued in counterpart European Application No. 13 747 807.9-1109 dated Oct. 2, 2018.
Hamada et al.; JP 2010173990A; Aug. 12, 2010 (Machine-English Translation).
International Preliminary Report on Patentability of Corresponding PCT/EP2012/065733 dated Oct. 3, 2014.
International Search Report of corresponding PCT/EP2013/065733 dated Sep. 26, 2013.

* cited by examiner

*Primary Examiner* — Shaojia A Jiang
*Assistant Examiner* — Michael C Henry
(74) *Attorney, Agent, or Firm* — Silvia Salvadori, P.C.; Silvia Salvadori

(57) ABSTRACT

The present invention relates to the use of chondroitin as a transdermal carrier and slow-release system for active ingredients in pharmaceutical and cosmeceutical compositions.

5 Claims, No Drawings

CHONDROITIN COMPLEXES FOR TRANSCUTANEOUS ABSORPTION

This Non-Provisional application is a Divisional application of U.S. application Ser. No. 14/416,669 filed on Jan. 23, 2015, which is a U.S. National Stage of PCT/EP2013/065733, filed on Jul. 25, 2013, which claims priority to and the benefit of Italian Application No. MI2012A001316 filed on 27 Jul. 2012, the contents of which are incorporated herein by reference in their entireties.

The present invention relates to the use of chondroitin as a transdermal carrier and slow-release system for active ingredients in pharmaceutical and cosmeceutical compositions.

Definitions

The term chondroitin is often used improperly to indicate chondroitin sulphate; for the sake of clarity, therefore, the two terms "chondroitin" and "chondroitin sulphate" will be used separately hereafter. The term "chondroitin" means the non-sulphated polysaccharide and the salts thereof, while the term "chondroitin sulphate" means the differently sulphated polysaccharide and the salts thereof.

PRIOR ART

Chondroitin, the metabolic precursor of chondroitin sulphate, is a natural linear polysaccharide formed by alternating residues of N-acetyl-D-galactosamine β 1:4 and D-glucuronate β 1:3. In vertebrates, chondroitin is sulphated regioselectively at the 4 or 6 hydroxyls of N-acetyl-D-galactosamine, and in some cases the 2 or 3 hydroxyls of glucuronic acid (Sugahara et al., J. Biol. Chem., 1996, 271:26745-54). The molecular weight of chondroitin, and the extent and sites of sulphation, depend on species, age and tissue type (Kuettner et al., Eds., in Articular cartilage and osteoarthritis, NY, Raven Press, 1992; Volpi Ed., in Chondroitin sulfate: structure, role and pharmacological activity, S. Diego, Calif. Academic Press—Elsevier Inc, 2006).

As chondroitin is a metabolic intermediate in vertebrates (Sugumaran and Silbert, J. Biol. Chem. 1990, Oct. 25, 265(30):18284-8), it cannot be isolated from animal sources in significant quantities. Processes for the production of chondroitin from micro-organisms or by enzymatic synthesis were only described recently.

The production of chondroitin by an engineered strain of E. coli K4, described in WO 2010136435, is particularly interesting; said strain produces polysaccharide K4, a chondroitin derivative that presents β-fructofuranose residues in the C3 position of glucuronic acid. These residues can easily be removed by controlled acid hydrolysis, due to the low stability of the glycoside bond with which the fructose is linked to the chondroitin chain. Using this micro-organism and an integrated strategy based on optimisation of a three-phase fermentation process (batch-fed batch-in microfiltration regimen), chondroitin yields of >8 g/L are obtained. The high production yields, simplicity of the downstream purification process, low overall process costs and low environmental impact make the process described in WO 2010136435 superior to all the fermentation strategies previously described (Rodriguez et al., Eur. J. Biochem., 1988, 177:117-124; Manzoni et al., Biotechnology Letters, 1996, 18:383-386; WO 01/02597 A1; U.S. Pat. Nos. 6,288,044; 6,777,398; US 2005266460; WO 0180810; EP 1282684; EP 1832662; US 20030104601; US 20050164984; US 20070015249; US 20030109693; EP 1950308; WO 2007145197; WO 2007069693; WO 2007058252; WO 2007058252; WO 2007023867; U.S. Pat. No. 7,273,729; JP 2004024208; US 20060052335; US 20060057697; U.S. Pat. No. 7,232,676; and US 20070059805).

More recently, US 2011244520A1 described a series of engineered micro-organisms which produce chondroitin in concentrations comparable with those of WO 2010136435.

As regards the enzymatic synthesis of chondroitin, US 2005266460, WO 0180810, EP 1282684, EP 1832662, US 20030104601 and US 20050164984 describe the use of chondroitin synthetase from Pasteurella multocida, an enzyme that catalyses the synthesis of chondroitin from the corresponding UDP sugars. US 20070015249 and US 20030109693 disclose the production of a chondroitin synthetase from E. coli K4 and its use for the production of chondroitin in vitro.

EP 1950308, WO 2007145197, WO 2007069693, WO 2007058252, WO 2007058252 and WO 2007023867 disclose in vitro methods of synthesising chondroitin and derivatives which use chondroitin synthetase from E. coli K4 and mutants thereof, which only present one of the two transferase activities.

U.S. Pat. No. 7,273,729, JP 2004024208, US 20060052335, US 20060057697 and U.S. Pat. No. 7,232,676 describe the use of human chondroitin synthetase, an enzyme that catalyses the synthesis of chondroitin from the corresponding UDP sugars. The documents describe the structure of human chondroitin synthetase, an expression vector that comprises the enzyme sequence, the expression of said vector in eukaryotic cells, and a method for synthesising the polysaccharide chain of chondroitin.

US 20070059805 discloses the structure of human chondroitin synthetase, an expression vector that comprises the enzyme sequence, the expression of said vector in eukaryotic cells, and a method for synthesising the polysaccharide chain of chondroitin.

All the documents cited above consider chondroitin to be an intermediate for chondroitin sulphate synthesis. Some of them do mention the possibility of using chondroitin in unspecified compositions, but only generically, as in the case of US 20110244520 (claim 63) and WO 0180810 (claim 73); this last document defines chondroitin, on pp. 4-5, as a polymer which is "more inert, loosely speaking, than the analogous HA molecule".

Hyaluronic acid is the only glycosaminoglycan for which the use as a carrier of active ingredients has been proposed. There is a great deal of scientific and patent literature on the subject which documents, though not always consistently, the ability of hyaluronic acid to permeate the skin and the walls of the mucous membranes, with some critical factors regarding the molecular weight.

The transcutaneous transport of diclofenac by hyaluronic acid has been extensively studied in vivo and in clinical trials (Brown et al. 2002, in Hyaluronan: Biomedical, Medical and Clinical Aspects, eds. J. Kennedy, G. O. Phillips, P. A. Williams, and V. Hascall, 249-256. Cambridge: Woodhead Publishers; Brown et al. 1995, in Hyaluronan in Drug Delivery, ed. D. A. Willoughby, 48-52. London: Royal Society of Medicine Press; Brown et al. 1995, in Hyaluronan in Drug Delivery, ed. D. A. Willoughby, 53-71, London: Royal Society of Medicine Press; Brown et al., 1995, Int. J. Tissue Reactions—Exp. Clin. Aspects 17:133-140; Brown and Moore, 1996, in Hyaluronan in Drug Delivery, ed. D. A. Willoughby, 121-131. London: Royal Society of Medicine Press; McEwan, and Smith, 1997, Aust. J. Derm. 38:187-189; Nazir et al., 2001, Pharm. Sci. 3(suppl.):1429).

These studies, as a whole, have demonstrated that in vitro, hyaluronic acid significantly improves the absorption of diclofenac into human skin, although it remains localised in the epidermis (McEwan and Smith, 1997, Aust. J. Derm. 38:187-189; Wolf et al., 2001, Int. J. Dermatol. 40:709-713; Brown et al., 1995, in Hyaluronan in Drug Delivery, ed. D. A. Willoughby, 53-71, London: Royal Society of Medicine Press; Brown, et al., 1995, in Hyaluronan in Drug Delivery, ed. D. A. Willoughby, 48-52. London: Royal Society of Medicine Press; Lin and Maibach, 1996, In Hyaluronan in Drug Delivery, ed. D. Willoughby, 167-174. London: R. S. M. Press; Brown, et al; 1999, J. Invest. Dermatol. 113:740-746).

Similar behaviour of hyaluronic acid, with localisation of the medicament in the epidermis, is reported for other active ingredients such as ibuprofen (Brown et al., in Hyaluronan: Biomedical, Medical and Clinical Aspects, eds. J. Kennedy, G. O. Phillips, P. A. Williams, and V. Hascall, 249-256. Cambridge: Woodhead Publishers; Brown and Martin, 2001, Int. J. Pharm. 225:113-121), clindamycin phosphate (Amr, 2000, Proc. Millen. Cong. Pharma. Sci. A80) and cyclosporin (Brown and Moore, 1996, in Hyaluronan in Drug Delivery, ed. D. A. Willoughby, 121-131. London: Royal Society of Medicine Press; Nazir et al., 2001, Pharm. Sci. 3(suppl.):1429).

On the basis of these rationales, U.S. Pat. Nos. 5,639,738 and 5,792,753 claim the combination of hyaluronic acid with a molecular weight of between 150 and 750 KDa and NSAIDs for the treatment of actinic keratosis, and U.S. Pat. No. 5,852,002 claims the combination of hyaluronic acid with a molecular weight of between 150 and 750 KDa with antibiotics, antibacterials, antimicrobials and combinations thereof for the treatment of infections.

Comparative studies based on the use of the Franz cell equipped with human skin demonstrate that only hyaluronic acid is able to transport diclofenac and ibuprofen in the skin, whereas other glycosaminoglycans, like chondroitin sulphate and heparin, are not (Brown et al., 2001, International J. of Pharmaceutics, 225, 113-121).

Solaraze® gel, based on hyaluronic acid and diclofenac, has obtained regulatory approval in the USA, Canada and Europe for the treatment of actinic keratosis.

DESCRIPTION OF THE INVENTION

It has surprisingly been found that unlike the findings reported for chondroitin sulphate, chondroitin with a molecular weight of between 5 and 100 KDa, when applied to the skin in suitable formulations, crosses the stratum corneum, permeates the epidermis and is carried into the body by the bloodstream.

The invention therefore relates to the use of chondroitin as a transdermal carrier and slow-release system for active ingredients in pharmaceutical and cosmeceutical compositions.

A further object of the invention is non-covalent complexes of non-sulphated chondroitin with active ingredients which are absorbed through the skin and the mucous membranes. Said complexes act as slow-release systems for the active ingredient.

Examples of active ingredients usable according to the invention are steroidal and non-steroidal anti-inflammatory drugs, antitumorals, antivirals, antimicrobials, diuretics, contraceptives, analgesics, bronchodilators, monoclonal antibodies, immunosuppressants, vasoconstrictors or vasodilators, antioxidants, soothing agents, moisturising agents, drainage agents, biostimulants, radical scavengers, wrinkle treatment agents, hair growth compounds and bioactive peptides, used individually or in combination with each other.

In general, non-covalent complexes of chondroitin with active ingredients are prepared by adding the active ingredient to aqueous or aqueous-organic solutions of chondroitin. To obtain the complex in solid form, the solvent is removed by evaporation under vacuum or by freeze-drying. The molar ratios between the active ingredient and the chondroitin monomer unit can vary within very wide limits: for example from 0.05 to 1 mole of active ingredient per monomer unit, depending on the recommended doses of the active ingredients in question.

The complexes thus obtained are therefore formulated using conventional techniques and excipients, in suitable compositions, in particular for the topical, nasal, rectal or vaginal administration. Said compositions, which are a further object of the invention, can optionally also contain other ingredients. The compositions of the invention can take the form of solutions, emulsions, gels, creams, sprays, suppositories, eyedrops, masks, patches, dressings or sticking plasters.

The formulations of the invention can also be obtained directly from the solution of the complex by adding emulsifiers, stabilisers, surfactants, preservatives and perfumes, depending on the type of product to be obtained (creams, gels, W/O or O/W emulsions, milks, masks, etc).

The transcutaneous absorption of chondroitin was evaluated using chondroitin tritium-labelled chondroitin obtained by biosynthesis and Charles River nude mice. The study demonstrates that chondroitin, when administered topically, regardless of its molecular weight, is effectively absorbed through the skin, and then distributed by the bloodstream throughout the body. 1 h after application, about 50% of the dose applied is localised in the skin, and only a minimal part is distributed in the body. After longer times the cutaneous absorption further increases, as does the process of systemic distribution through the bloodstream. After 20 h, about 25% of the radioactivity administered has been excreted with the urine.

It has also been found that chondroitin acts as a slow-release system for active ingredients. In fact, its structural characteristics make interaction with low-molecular-weight molecules possible via different kinds of forces of attraction, which can act individually or synergically, such as complementary ionic interactions, hydrophobic and hydrophilic interactions, and hydrogen bridges. Said interactions break down in aqueous solutions, but re-form continually due to the presence, at a usable distance, of new possibilities of interaction with different sites on the same polymer chain. Such behaviour in practice reduces the mobility of the bonded compound, which remains trapped for a long time in a cage of attraction forces generated by the polymer chain. The non-covalent complex obviously resolves gradually with time in an open system, with kinetics that depend on the state of dilution and the presence of other chemical species.

A dialysis equilibrium study, wherein the solution of the complex is enclosed in a dialysis tube with a 2 KDa cut-off, with a volume of water 20 times greater on the outside, demonstrates that in this experimental system, diclofenac-chondroitin complexes with different stoichiometries act as systems for the controlled release of the active ingredient, reaching dialysis equilibrium in times exceeding 10 h, which become slower as the diclofenac-chondroitin ratio in the complex reduces. In the system wherein only diclofenac is present, dialysis equilibrium is already reached after 2 h.

The simultaneous ability of chondroitin to cross the stratum corneum of the skin and the surface of the mucous membranes, combined with the ability to form non-covalent complexes, therefore makes this polysaccharide an excellent carrier of various kinds of active ingredients in humans.

In vitro studies on human skin in a Franz cell demonstrate the carrier effect and the release mechanism of chondroitin when it forms non-covalent complexes with different active ingredients, such as diclofenac and ketorolac. The same findings are obtained with studies involving topical applications of said complexes to nude mice.

The following examples describe the invention in more detail.

Example 1—Preparation of [$^3$H]Chondroitin with Different Molecular Weights

[$^3$H]Chondroitin was obtained by biosynthesis using, as described in WO 2010136435, an engineered strain of *E. coli* K4 which produces polysaccharide K4, a chondroitin derivative which, at the C3 position of glucuronic acid, presents β-fructofuranose residues that are eliminated quantitatively by mild hydrolysis with acetic acid. [$^3$H]galactose is added to the culture medium to radiolabel the chondroitin. [$^3$H]chondroitin, purified as described in WO 2010136435, has a molecular weight of 62 KDa. For use in the subsequent study it was diluted with non-labelled chondroitin of the same molecular weight to give a product with a specific radioactivity of $1.5 \times 10^7$ dpm/mg. To obtain chondroitin with a molecular weight of 35 and 10 KDa, [$^3$H]chondroitin MW 62 KDa, with a specific radioactivity of $1.5 \times 10^7$ dpm/mg, was subjected to controlled acid hydrolysis in heterogeneous phase. In a standard procedure, 100 mg of [$^3$H]chondroitin was suspended in 1 mL of ethanol (93% v/v) containing 33 μL of HCl, and incubated under stirring in a Vortemp at 55° C. and 900 rpm. Hydrolysis was conducted for 40 min to obtain a MW of 35 KDa and 90 min to obtain a MW of 10 KDa. When the desired MW had been reached, the reaction was stopped in ice, neutralising with 21 μL of 50% w/v NaOH, then left under stirring for 30 min and centrifuged at 5,000 rpm for 15 min. The supernatant was removed and the precipitated residue washed with 1 mL of ethanol (93% v/v). The washing operation was repeated a second time using anhydrous ethanol. After centrifugation the pellet was dried for 16 h in a stove at 40° C. under vacuum. The chondroitin molecular weight analysis was conducted with a size-exclusion chromatography system equipped with a multi-detector, consisting of a four-bridge viscometer, a refractometer, a right-angle light-scattering detector (RALS) and a low-angle light-scattering detector (LALS), patented by the American Viscotek group (www.viscotek.com). The signal measured with LALS is proportional to the molecular weight and concentration, and the signal measured with the viscometric detector is proportional to the concentration of the sample and the intrinsic viscosity, while the refractometer measures the concentration. The Viscotek apparatus not only determines the molecular weight, but also allows evaluation of the degree of heterogeneity of the molecular weight in the population of molecules present, described by the polydispersity index Mw/Mn, automatically calculated by the Viscotek apparatus, and defined as the ratio between the average molecular weight ($Mw=\Sigma_i m_i M_i/\Sigma_i m_i$ wherein $m_i$ is the mass of polymer with molecular weight $M_i$ and $\Sigma_i m_i$ is the total mass of the polymer, which said expression, assuming $m_i=n_i M_i$, can also be presented as $Mw=\Sigma_i n_i M_i^2/\Sigma_i n_i M_i$) and weight average molecular weight ($Mn=\Sigma_i n_i M_i/\Sigma_i n_i$ wherein $n_i M_i$ is the polymer mass with molecular weight Mi and $\Sigma$i ni is the total number of moles of polymer present). The polydispersity value in the samples of [$^3$H]chondroitin with different molecular weights (62, 35 and 10) did not exceed 1.2.

To test the specificity of the labelling site, a sample of [$^3$H]chondroitin was subjected to strong acid hydrolysis in aqueous solution at 100° C. to cause the total rupture of the glycoside bonds. A sample of the hydrolysis mixture was analysed by HPLC. A Carbopac PA1 4×250 mm analytical column fitted with a Carbopac PA1 4×50 mm precolumn (Dionex Srl, San Donato Milanese, Italy), operating at a flow rate of 1 mL/min, was used for the quantitation of GlcA, GalNAc and GalNH. The standards and the samples were analysed according to a gradient separation method with the following eluents: Eluent A 150 mM NaOH, Eluent B 150 mM NaOH+1M Na acetate. The gradient used was (Time in min, % eluent A, % eluent B): T0, A90, B10; T20, A80, B20; T30, A50, B50; T35, A90, B10; T40, A100, B0). Detection was effected with a pulsed ammeter detector (AgCl reference electrode) with Waveform Carbohydrates. The hydrolysis mixture resolved into three peaks, corresponding to the retention times of glucuronic acid, galactosamine and traces of N-acetyl-D-galactosamine. The eluates at the peaks were collected and read for radioactivity in scintillation fluid. 75% of the radioactivity was associated with the peaks of galactosamine and N-acetyl-D-galactosamine.

Three [$^3$H]chondroitin gels, each containing 100 mg of polyethylene glycol, 1 mg of benzyl alcohol, 879 mg of water and 20 mg of [$^3$H]chondroitin ($3 \times 10^8$ dpm) per gram, with a MW of 62, 35 and 10 KDa respectively, were prepared for the subsequent study on the animal model.

Example 2—Topical Absorption of Chondroitin with Different Molecular Weights 60 five-month-old Charles River nude mice of both sexes were used as experimental model to evaluate the transcutaneous absorption of chondroitin. The animals were randomised into 12 groups of 5 which, as reported in the study design in table 1, were treated with 50 mg of [$^3$H]chondroitin gel with different MWs, prepared as described in example 1. During the study the animals were kept in individual cages, with unrestricted access to food and water.

The animals were euthanised 1, 5, 10 and 20 h after the application, as reported in the trial design in table 1. Immediately after euthanisation the gel application area was thoroughly washed until no detectable traces of radioactivity remained in the washing water, in order to discriminate between the radioactivity applied and the radioactivity absorbed by the skin. The treated skin areas, liver and blood were recovered from the euthanised animals, and the samples were weighed and frozen immediately after removal. The urine of the animals was recovered from the cages by washing.

TABLE 1

Trial design: 60 five-month-old Charles River nude mice of both sexes were randomised into 12 groups of 5 animals. An area of about 5-6 cm² was marked on the back of each animal, in a position where it was difficult for the animals to lick or scratch themselves. 50 mg of [³H]chondroitin gel MW 62 KDa was applied with a spatula for animals 1 to 20, MW 35 KDa for animals 21 to 40, and MW 10 KDa for animals 41 to 60.

| animals | treatment | time of euthanasia (h) |
|---|---|---|
| 1-5 | [³H]chondroitin MW 62 KDa | 1 |
| 6-10 | | 5 |
| 11-15 | | 10 |
| 16-20 | | 20 |
| 21-25 | [³H]chondroitin MW 35 KDa | 1 |
| 26-30 | | 5 |
| 31-35 | | 10 |
| 36-40 | | 20 |
| 41-45 | [³H]chondroitin MW 10 KDa | 1 |
| 46-50 | | 5 |
| 51-55 | | 10 |
| 56-60 | | 20 |

Skin, liver and blood samples (150-200 mg) were solubilised in Soluene for h at ambient temperature. The radioactivity was measured by liquid-phase scintillation on the solubilised samples and the urine. The experimental data are reported in tables 2-4.

TABLE 2

Distribution of radioactivity in nude mice treated topically with a [³H]chondroitin gel (3 × 10⁸ dpm) MW 62 KDa. Each figure represents the average of 5 animals.

| Sample | 1 h | 5 h | 10 h | 20 h |
|---|---|---|---|---|
| | | % of dose applied | | |
| skin | 52 ± 10 | 73 ± 14 | 50 ± 12 | 5 ± 2 |
| liver | 0.1 ± 0.04 | 2.2 ± 0.5 | 3.1 ± 0.3 | 1.1 ± 0.2 |
| blood | 0.5 ± 0.1 | 8.2 ± 1.3 | 6.9 ± 2.1 | 3.1 ± 1.6 |
| urine | — | 2.3 ± 1.2 | 5.9 ± 4.3 | 24.8 ± 10.2 |

TABLE 3

Distribution of radioactivity in nude mice treated topically with a [³H]chondroitin gel (3 × 10⁸ dpm) MW 35 KDa. Each figure represents the average of 5 animals.

| Sample | 1 h | 5 h | 10 h | 20 h |
|---|---|---|---|---|
| | | % of dose applied | | |
| skin | 49 ± 8 | 74 ± 10 | 53 ± 13 | 8 ± 3 |
| liver | 0.1 ± 0.02 | 2.0 ± 0.7 | 3.4 ± 0.5 | 1.3 ± 0.4 |
| blood | 0.7 ± 0.2 | 8.8 ± 1.9 | 6.6 ± 2.4 | 3.8 ± 1.5 |
| urine | — | 2.6 ± 1.3 | 7.1 ± 4.0 | 26.3 ± 11.4 |

TABLE 4

Distribution of radioactivity in nude mice treated topically with a [³H]chondroitin gel (3 × 10⁸ dpm) MW 10 KDa. Each figure represents the average of 5 animals.

| Sample | 1 h | 5 h | 10 h | 20 h |
|---|---|---|---|---|
| | | % of dose applied | | |
| skin | 58 ± 0.9 | 78 ± 15 | 51 ± 9 | 6.2 ± 1.9 |
| liver | 0.1 ± 0.04 | 2.2 ± 0.6 | 3.8 ± 0.5 | 1.4 ± 0.3 |
| blood | 0.9 ± 0.2 | 8.2 ± 1.4 | 6.9 ± 3.4 | 3.3 ± 1.3 |
| urine | — | 2.5 ± 1.9 | 6.1 ± 3.3 | 24.9 ± 13.2 |

The data demonstrate that chondroitin, when administered topically, is effectively absorbed through the skin, and then distributed by the bloodstream throughout the body, regardless of its molecular weight. 1 h after application, about 50% of the dose applied is localised in the skin, and only a minimal part is distributed in the body. After longer times the cutaneous absorption further increases, as does the process of systemic distribution through the bloodstream. After 20 h, about 25% of the radioactivity administered has been excreted with the urine.

Example 3—Preparation of Non-Covalent Diclofenac-Chondroitin Complexes with Different Stoichiometric Compositions Preparation of chondroitin complex with 2-(2-[2,6-dichlorophenylamino]phenyl) ethanoic acid, also called diclofenac.

Diclofenac-chondroitin complexes were prepared with molar ratios of 0.630, 0.315 and 0.063 between diclofenac and the chondroitin monomer unit.

Preparation of diclofenac-chondroitin complex with a molar ratio of 0.630-5 g of diclofenac sodium was dissolved at 50° C. under vigorous stiffing in 100 mL of a 10% w/v aqueous solution of chondroitin sodium MW 62 KDa.

Preparation of diclofenac-chondroitin complex with a molar ratio of 0.315-2.5 g of diclofenac sodium was dissolved at 50° C. under vigorous stiffing in 100 mL of a 10% w/v aqueous solution of chondroitin sodium MW 35 KDa.

Preparation of diclofenac-chondroitin complex with a molar ratio of 0.063-0.5 g of diclofenac sodium was dissolved at 50° C. under vigorous stiffing in 100 mL of a 10% w/v aqueous solution of chondroitin sodium MW 10 KDa.

The solid forms of said complexes were obtained by removing the solvent under vacuum at 50° C., or alternatively by freeze-drying the solutions. The solid complexes solubilise rapidly in water.

Example 4—In Vitro Studies of Gradual Release of Diclofenac from Non-Covalent Diclofenac-Chondroitin Complexes with Different Stoichiometries To evaluate the release mechanism of diclofenac from non-covalent complexes with chondroitin of different stoichiometries differentially, a dialysis equilibrium study was designed wherein the solution of the complex is enclosed in a dialysis tube with a 2 KDa cut-off, and an external water volume 20 times greater. The system was maintained under continuous stirring at 25° C., and the absorption was read over time at 275 nm, at which diclofenac presents the maximum absorption. In this way, as only diclofenac can cross the dialysis membrane, in view of the considerable difference in volume between the dialysed solution and the dialysis medium, the increased absorption at 275 nm can be attributed to the quantity of diclofenac released from the complex with chondroitin. Table 5 shows the study data.

TABLE 5

Dialysis equilibrium study, wherein 100 mL of aqueous solution of the complex was present in a dialysis tube with a 2 KDa cut-off, with a 2 L external water volume. The system was maintained under continuous stirring at 25° C., and the absorption was read over time at 275 nm, at which diclofenac presents the maximum absorption.

| Stoichiometry of complex (moles of diclofenac/moles of chondroitin) | % $OD_{275}$* present at different times (h) in the dialysis medium | | | | |
|---|---|---|---|---|---|
| | 1 | 2 | 4 | 8 | 16 |
| 0.630 | 30 | 48 | 71 | 82 | 95 |
| 0.315 | 21 | 33 | 56 | 68 | 91 |
| 0.063 | 13 | 20 | 45 | 59 | 79 |
| Diclofenac only** | 85 | 94 | 96 | 95 | 96 |

*Taking the $OD_{275}$ present in the diclofenac-chondroitin complex in the dialysis tube as 100, the total percentage of $OD_{275}$ recovered in the dialysis solution at different times is reported;
**100 mL of aqueous solution containing 5% w/v of diclofenac sodium salt was introduced into the dialysis tube.

The study demonstrates that in this experimental system, diclofenac-chondroitin complexes with different stoichiometries behave as systems for the controlled release of the active ingredient, reaching dialysis equilibrium in times exceeding 10 h, which lengthen as the diclofenac-chondroitin ratio in the complex falls. In the system wherein only diclofenac is present, dialysis equilibrium is already reached after 2 h.

Example 5—In Vitro Studies of Transcutaneous Absorption of Non-Covalent Diclofenac-Chondroitin Complexes The study was conducted using a Franz cell equipped with a human skin sample originating from plastic surgery for breast reduction on a healthy 45-year-old woman. The skin was frozen to −20° C. immediately after removal, and kept at that temperature until the time of use. Before being placed in the Franz cells, the frozen skin was cleaned of subcutaneous fat, so that only the stratum corneum, the epidermis and the dermis were used, and cut to a size suitable for positioning in the Franz cell, with the stratum corneum facing upwards. Before the study began, the cell was maintained at 30° C. for 10 h with continual stirring of the receptor solution consisting of 10 mL of HBSS (Hank's Buffered Saline Solutions). The surface on which the formulation was deposited measured about 3 cm². Before application of the gel in the cells, the receptor solution was replaced, taking care to eliminate all air bubbles between skin and solution. 10 mg of the following gels was applied to the skin surface: a) diclofenac gel (per gram of gel: 100 mg of polyethylene glycol, 1 mg of benzyl alcohol, 200 mg of diclofenac sodium and water q.s. for 1 g, dissolved at 50° C. under vigorous stirring); b) diclofenac-chondroitin gel (0.630 moles of diclofenac/mole of chondroitin disaccharide units; per gram of gel: 100 mg of polyethylene glycol, 1 mg of benzyl alcohol, 200 mg of chondroitin MW 35 KDa, 100 mg of diclofenac sodium and water q.s. for 1 g, dissolved at 50° C. under vigorous stirring); c) diclofenac-chondroitin gel (0.630 moles of diclofenac/mole of chondroitin sulphate disaccharide units; per gram of gel: 100 mg of polyethylene glycol, 1 mg of benzyl alcohol, 279.6 mg of chondroitin MW 35.4 KDa, 100 mg of diclofenac sodium and water q.s. for 1 g, dissolved at 50° C. under vigorous stirring).

At the indicated times the receptor phase was recovered and the skin surface was washed thoroughly to remove all the unabsorbed gel. The skin was recovered, homogenised and digested for 10 h under stirring at 30° C. with collagenase (5,200 I/g of skin) in 10 mM of phosphate buffer pH 7.4. At the end of the incubation, 0.4 volumes of ethanol were added and the mixture was centrifuged at 10,000 rpm for 20 min. Under these conditions, almost all the diclofenac present in the tissue is extracted in the solution. The quantity of diclofenac present in the skin washing solution (unabsorbed part), in the enzymatic tissue digestate (part absorbed through the skin) and in the receptor fluid (part that crossed the skin structure) was quantitatively determined by HPLC. The analyses were performed on a Waters model 746 HPLC (USA), equipped with a μ-bondapack C18 column (150×4.6 millimetres). A solution of acetonitrile, deionised water and orthophosphoric acid (45:54.5:0.5 in vol.) was used as mobile phase with a final pH of 3.5, operating with a flow rate of 1 mL/min. The eluate was monitored at 276 nm. Quantitation was obtained by measuring the ratios between the peak area of diclofenac and the peak area of the internal standard consisting of a naproxen solution with a known titre.

Table 6 shows the results of the study.

TABLE 6

Study of absorption of diclofenac by human skin using the Franz cell.

| Sample of gel containing | time (h) | % of diclofenac dose applied | | |
|---|---|---|---|---|
| | | on the skin* | in the skin | in the receptor fluid |
| Diclofenac | 1 | 96 | 2 | 0 |
| | 5 | 91 | 3.5 | 0.9 |
| | 10 | 89 | 3.1 | 1.8 |
| Diclofenac-chondroitin | 1 | 82 | 11.4 | 3.8 |
| | 5 | 75 | 18.2 | 7.5 |
| | 10 | 69 | 16.5 | 11.9 |
| Diclofenac-chondroitin sulphate | 1 | 98 | nd | Nd |
| | 5 | 95 | 2.7 | 1.1 |
| | 10 | 91 | 2.9 | 1.6 |

*quantity of diclofenac present at the end of the study in the solution used to wash the surface of the skin mounted in the Franz cell.

As will be seen from analysis of the data in table 6, the absorption of diclofenac in the presence of chondroitin increases significantly compared with the absorption observed in the absence of the polysaccharide or in the presence of chondroitin sulphate.

Example 6—In Vivo Studies of Transcutaneous Absorption of Chondroitin-Diclofenac Complexes 45 five-month-old Charles River nude mice of both sexes were used as experimental model to evaluate the transcutaneous absorption of the diclofenac-chondroitin complex. The animals were randomised into 9 groups of 5 which, as reported in the trial design in table 7, were treated with 50 mg of the three gels: a) diclofenac gel; b) diclofenac-chondroitin gel; and c) diclofenac chondroitin sulphate gel, prepared as reported in example 5. During the study the animals were kept in individual cages, with unrestricted access to food and water.

TABLE 7

Trial design: 45 five-month-old Charles River nude mice of both sexes were randomised into 9 groups of 5 animals. An area of about 5-6 cm² was marked on the back of each animal, in a position where it was difficult for the animals to lick or scratch themselves. 50 mg of diclofenac gel was applied to said area with a spatula for animals 1 to 15, 50 mg of diclofenac-chondroitin gel for animals 16 to 30, and 50 mg of diclofenac chondroitin sulphate gel for animals 31 to 45.

| animals | Treatment | time of euthanasia (h) |
|---|---|---|
| 1-5 | Diclofenac gel | 1 |
| 6-10 | | 5 |
| 11-15 | | 10 |
| 16-20 | Diclofenac-chondroitin gel | 1 |
| 21-25 | | 5 |
| 26-30 | | 10 |
| 31-35 | Diclofenac-chondroitin sulphate gel | 1 |
| 36-40 | | 5 |
| 41-55 | | 10 |

The animals were euthanised 1, 5 and 10 h after the application, as reported in the trial design in table 7. Immediately after euthanisation the gel application area was washed thoroughly to discriminate between the radioactivity applied and the radioactivity absorbed by the skin. The treated skin areas, liver and blood were recovered from the euthanised animals, and the samples were weighed and frozen immediately after removal. The urine of the animals was recovered from the cages by washing. The skin and liver samples were solubilised by enzymatic treatment with collagenase, and the quantity of diclofenac present was determined by HPLC as reported in example 5. The diclofenac content in the serum and in urine was similarly determined by HPLC.

The experimental data are reported in tables 8-10.

TABLE 8

Distribution of radioactivity in nude mice treated topically with diclofenac gel. Each figure represents the average of 5 animals.

| | Time of euthanasia (h) | | |
|---|---|---|---|
| | 1 | 5 | 10 |
| | % of dose applied | | |
| skin | 0.8 ± 0.3 | 1.2 ± 0.5 | 3 ± 0.4 |
| liver | Nd | nd | 0.1 ± 0.03 |
| serum | Nd | nd | 0.5 ± 0.12 |
| urine | Nd | nd | 0.9 ± 0.3 |

TABLE 9

Distribution of radioactivity in nude mice treated topically with diclofenac-chondroitin gel. Each figure represents the average of 5 animals.

| | Time of euthanasia (h) | | |
|---|---|---|---|
| Sample | 1 | 5 | 10 |
| | % of dose applied | | |
| skin | 49 ± 13 | 69 ± 15 | 45 ± 10 |
| liver | Nd | 1.2 ± 0.3 | 3.1 ± 0.7 |
| serum | 0.9 ± 0.3 | 6.1 ± 1.4 | 3.1 ± 1.1 |
| urine | Nd | 1.9 ± 1.5 | 7.9 ± 5.1 |

TABLE 10

Distribution of radioactivity in nude mice treated topically with diclofenac-chondroitin sulphate gel. Each figure represents the average of 5 animals.

| | Time of euthanasia (h) | | |
|---|---|---|---|
| Sample | 1 | 5 | 10 |
| | % of dose applied | | |
| skin | 2 ± 1 | 3 ± 1.5 | 7 ± 2.3 |
| liver | nd | nd | 1.1 ± 0.4 |
| serum | nd | 1.0 ± 0.3 | 0.9 ± 0.3 |
| urine | nd | 0.3 ± 0.1 | 2.1 ± 1.3 |

The data in tables 8-10 demonstrates that chondroitin, but not chondroitin sulphate, acts as an efficient transdermal carrier of diclofenac, which is not only found localised in the skin, but also distributed systemically. Diclofenac alone has a transcutaneous absorption far lower than that observed in the case of the non-covalent complex with chondroitin.

Example 7—In Vitro Studies of Transcutaneous Absorption of Non-Covalent Ketorolac-Chondroitin Complexes (±)-5-benzoyl-2,3-dihydro-1H-pyrrolizine-1-carboxylic acid or tromethamine ketorolac salt, better known by the tradename toradol, is an NSAID widely used as an anti-inflammatory, despite the major side effects connected with its long-term use. The study of the topical absorption of this active ingredient, as a non-covalent complex with chondroitin, was conducted according to the procedure described in example 5, using a Franz cell equipped with a human skin sample originating from plastic surgery for breast reduction on a healthy 33-year-old woman. 10 mg of the following gels was applied to the skin surface: a) tromethamine ketorolac salt gel (per gram of gel: 100 mg of polyethylene glycol, 1 mg of benzyl alcohol, 200 mg of tromethamine ketorolac salt and water q.s. for 1 g, dissolved at 50° C. under vigorous stirring); b) tromethamine ketorolac salt-chondroitin gel (0.535 moles of tromethamine ketorolac salt/mole of disaccharide chondroitin units; per gram of gel: 100 mg of polyethylene glycol, 1 mg of benzyl alcohol, 200 mg of chondroitin MW 62 KDa, 100 mg of tromethamine ketorolac salt and water q.s. for 1 g, dissolved at 50° C. under vigorous stirring).

The sample treatment procedures were as reported in example 5. The quantity of ketorolac present in the skin washing solution (unabsorbed part), in the enzymatic tissue digestate (part absorbed by the skin) and in the receptor fluid (part that crossed the skin structure) was determined quantitatively by HPLC. The tests were conducted on a Waters model 746 (USA) HPLC, equipped with a μ-bondapack C18 column (150×4.6 millimetres). A solution of acetonitrile, deionised water and orthophosphoric acid (45:54.5:0.5 in vol.), with a final pH of 3.5, was used as mobile phase, operating with a flow rate of 1 mL/min. The eluate was monitored at 280 nm. Quantitation was performed by measuring the ratios between the peak area of ketorolac and the peak area of the internal standard, consisting of a naproxen solution with a known titre.

Table 11 shows the results of the study.

TABLE 11

Study of absorption of ketorolac by human skin using the Franz cell.

| Sample of gel containing | time (h) | % of diclofenac dose applied | | |
|---|---|---|---|---|
| | | on the skin* | in the skin | in the receptor fluid |
| Ketorolac | 1 | 98 | 1 | nd |
| | 5 | 93 | 2.6 | 0.7 |
| | 10 | 87 | 4.2 | 2.8 |
| Ketorolac-chondroitin | 1 | 85 | 9.4 | 4.8 |
| | 5 | 79 | 11.6 | 8.2 |
| | 10 | 70 | 14.2 | 10.8 |

*quantity of ketorolac present at the end of the study in the solution used to wash the surface of the skin mounted in the Franz cell.

As will be seen from analysis of the data in table 11, the absorption of ketorolac in the presence of chondroitin increases significantly compared with the absorption observed in the absence of the polysaccharide.

The invention claimed is:

1. A method of transdermal or trans-mucosa delivery of a non-covalent complex of non-sulphated chondroitin having a molecular weight between 5 and 100 kDa determined by size exclusion chromatography and an active ingredient in a patient in need thereof, said method comprising applying said complex on said skin or on said mucosa of said patient; and obtaining said transdermal or transmucosa delivery of said complex, wherein said complex is absorbed through mucous membranes or skin and wherein said complex behaves as transdermal carrier and slow-release system for said active ingredient.

2. The method according to claim 1, wherein the active ingredient is a non-steroidal or steroidal anti-inflammatory, an antitumoral, an antiviral, an antimicrobial, a diuretic, a contraceptive, an analgesic, a bronchodilator, a monoclonal antibody, an immunosuppressant, a vasoconstrictor or a vasodilator, an antioxidant, a soothing, moisturising or draining agent, a biostimulant, a radical scavenger, a wrinkle treatment agent, a hair growth compound or a bioactive peptide, or combinations thereof.

3. The method according to claim 1, wherein said complex is administered topically, nasally, rectally or vaginally.

4. The method according to claim 1 wherein said complex is in the form of solutions, emulsions, gel, creams, sprays, suppositories, eyedrops, masks, patches, dressings and plasters.

5. The method according to claim 1, wherein said non-sulphated chondroitin behaves as a transdermal carrier and slow-release system for said active ingredient.

* * * * *